US006462094B1

(12) United States Patent
Dang et al.

(10) Patent No.: US 6,462,094 B1
(45) Date of Patent: Oct. 8, 2002

(54) DECONGESTANT/EXPECTORANT COMPOSITIONS

(75) Inventors: Phuong Grace Dang, West Windsor; Alexander D. D'Addio, Piscataway, both of NJ (US)

(73) Assignee: Medpointe Healthcare Inc., Somerset, NJ (US)

( * ) Notice: Subject to any disclaimer, the term of this patent is extended or adjusted under 35 U.S.C. 154(b) by 0 days.

(21) Appl. No.: 09/938,149

(22) Filed: Aug. 22, 2001

(51) Int. Cl.$^7$ .......................... A01N 25/00; C07C 69/88
(52) U.S. Cl. .......................................... 514/849; 560/68
(58) Field of Search ................................ 514/646, 653, 514/849; 560/68

(56) References Cited

U.S. PATENT DOCUMENTS

| | | | | |
|---|---|---|---|---|
| 5,599,846 A | * | 2/1997 | Chopdekar et al. | 514/653 |
| 5,663,415 A | | 9/1997 | Chopdekar et al. | 560/68 |
| 6,037,358 A | | 3/2000 | Gordziel | 514/357 |
| 6,287,597 B1 | | 9/2001 | Gordziel | 424/464 |
| 2001/0011104 A1 | | 8/2001 | Gordziel | 514/653 |

FOREIGN PATENT DOCUMENTS

JP           64007786          8/1993

OTHER PUBLICATIONS

Pysician's Desk Reference, 33$^{rd}$ ed., pp. 1424–1425. (1979).*
Wilson and Gisvold's Textbook of Organic Medicinal and Pharmaceutical Chemistry, 9$^{th}$ ed. pp. 423 and 425.*
Weiler et al., "Randomized, double blind, parallel groups, placebo–controlled study of efficacy and safety of Rynatan in the treatment of allergic rhinits using an acute model," Annals of Allergy, vol. 64(1): 63–67.
Goldberg et al., "Evaluation of a Prolonged Action Oral Antihistaminic Preparation as Treatment for Allergic Disorders," Clinical Medicine, vol. 72(9): 1475–1479.
Triple Tannate, Drug Launches (doc. #: 0182701) 5/99.
Tussi–12, Drug Launches (doc. #: 0179128) 3/99.
Tussi–12, Drug Launches (doc. #: 0176901) 12/98.
R–Tannate, Drug Launches (doc. #: 0172212) 8/98.
Triple Tannate, Drug Launches (doc. #: 0163340). 1/98.
Atrohist, Drug Launches (doc. #: 0154800). 5/97.
Gelhist, Drug Launches (doc. #: 015445). 5/97.
Phenatan, Drug Launches (doc. #: 0149758) 1/97.
Triotann, Drug Launches (doc. #: 0136052) 12/95.
Tri–Tannate, Drug Launches (doc. #: 0129566) 6/95.
Ricobin–D, Drug Launches (doc. #: 0129564) 6/95.
Ricobid, Drug Launches (doc. #: 0129563) 6/95.
Quad–Tuss Tannate, Drug Launches (doc. #: 0127440) 4/95.
Tri–Tannate, Drug Launches (doc. #: 0179121) 3/99.
Tritan, Drug Launches (doc. #: 0144945) 9/96.
Tri–Natan, Drug Launches (doc. #: 0110372) 11/93.
R–Tannate, Drug Launches (doc. #: 0110158) 11/93.
Trin Tuss, Drug Launches (doc. #0049139) 3/93.
Tanoral, Drug Launches (doc. #: 0044406) 4/92.
Histatuss, Drug Launches (doc. #: 0041022) 7/91.
Tri–Tannate, Drug Launches (doc. #: 0020282) 9/87.

* cited by examiner

*Primary Examiner*—Mukund J. Shah
*Assistant Examiner*—Zachary C. Tucker
(74) *Attorney, Agent, or Firm*—Elliot M. Olstein; Raymond E. Stauffer

(57) ABSTRACT

Compositions consisting essentially of phenylephrine tannate and guaifenesin which are effective when administered orally for the symptomatic relief of cough associated with respiratory tract conditions such as the common cold, bronchial asthma, acute and chronic bronchitis are disclosed.

14 Claims, No Drawings

DECONGESTANT/EXPECTORANT COMPOSITIONS

FIELD OF INVENTION

The invention relates to novel decongestant/expectorant compositions containing two essential ingredients phenylephrine tannate and guaifenesin.

BACKGROUND OF INVENTION

A considerable number of tannic acids occur in nature. Chemically, these acids are described as polymers of different hydroxybenzoic acids. Generally, when the term tannic acid is employed, as in the present case, the acid referred to is gallotannic acid. The internal ester of gallic acid also frequently referred to as tannin.

Tannic acid consists of an amorphous powder, glistening scales, or spongy masses varying in color from yellowish-white to light brown. Tannic acid is very soluble in water or alcohol.

Tannic acids are usually obtained from glycosides which consist of several molecules of a tannic acid in combination with glucose.

Commercially available, tannic acid, also known as tannin, has a complex non-uniform chemistry, usually contains from about 5% to about 10% water by weight, has a molecular weight of about 1700, and is typically produced from Turkish or Chinese nutgall.

Phenylepherine, known chemically as 1-m-hydroxy-α-[(methylamino)methyl] benzyl alcohol, is a synthetic, optically active sympathomimetic amine which has one hydroxyl group on the benzene ring. The hydroxyl group is placed in the position meta to the aliphatic side chain. The meta position affords optimal activity and phenylepherine (neo-synephrine) replaced an older preparation, synephrine, in which the hydroxyl was in the para position.

Phenylephrine hydrochloride is available in the form of the levorotatory isomer, a white, odorless, non-hygroscopic, crystalline compound possessing a bitter taste. Phenylephrine hydrochloride has a melting point of 140–145° C. and is freely soluble in water and alcohol. Decongestant compounds in the form of their free bases as well as their salts, e.g. hydrochloride, citrate, maleate, tannate, etc., are well known. Decongestants in the form of their tannate salts are very desirable because such salts are generally stable.

Decongestants in the form of their tannate salts are typically prepared by reacting the free base, e.g. phenylephrine, etc. with tannic acid in the presence of a volatile solvent, usually isopropanol. Typically, in the conventional isopropanol route, the decongestant free base and the tannic acid will be present in the isopropanol at a concentration of about 20% based on the weight of the reaction mixture. The reaction mixture is stirred for about one hour while maintaining the mixture at 60–70° C. The reaction mixture is cooled to room temperature and then filtered, washed with isopropanol and then vacuum dried. Alternative routes to the tannate salts are described in U.S. Pat. No. 5,599,846 and U.S. Pat. No. 5,663,41 5.

Guaifenesin, known chemically as 3(2-methoxyphenoxy)-1,2-propanediol, is a crystalline powder soluble in water and alcohol. It is indicated in the USP Drug information as an expectorant for the symptomatic relief of cough due to colds and minor upper respiratory infections.

THE INVENTION

It has now been found that the novel combination of phenylephrine tannate and guaifenesin produces a composition possessing sympathornimetic decongestant and expectorant properties superior to the use of either one of the compounds alone. Guaifenesin has an expectorant action which increases the output of respiratory tract fluid by reducing adhesiveness and surface tension. The increased flow of less viscous secretions promotes ciliary action and facilitates the removal of mucus. This changes a dry, unproductive cough to one that is more productive and less frequent.

The compositions described herein are designed to be taken twice a day with the immediate expectorant action of guaifenesin and the prolonged decongestant action of phenylephrine tannate. The compositions of the present invention may be prepared for oral administration in the form of powders, capsules, elixirs, syrups and the preferred forms of tablets or suspensions.

Tablets containing the unique phenylephrine tannate and guaifenesin compositions of the present invention are prepared in a conventional manner by the addition of suitable pharmaceutical carriers including fillers, diluents, colorants, lubricants and the like, as well as conventional and well known binding and disintegrating agents. Each tablet would contain approximately 20 to 30 mg of phenylephrine tannate and 100 to 300 mg of guaifenesin. A typical tablet composition of the present invention containing starch, dibasic calcium phosphate, colorants, magnesium stearate, methylcellulose, polygalacturonic acid, povidone and talc, as described in Example 1 which follows, is prepared by well known conventional tabletting techniques such as those disclosed in U.S. Pat. Nos. 3,018,221; 2,798,024 arid 2,757, 124.

EXAMPLE 1

| Phenylephrine Tannate and Guaifenesin Tablets | |
|---|---|
| Ingredient | Milligrams per Tablet |
| Phenylephrine tannate | 25.00 |
| Guaifenesin | 200.00 |
| Starch, NF | 65.00 |
| Methylcellulose, USP | 150.00 |
| Polygalacturonic Acid | 32.00 |
| Dibasic Calcium Phosphate, USP, Dihydrate | 65.00 |
| Povidone, USP | 25.00 |
| Talc, USP | 5.40 |
| FD&C Red #40 Aluminum Lake-40% | 0.35 |
| Magnesium Stearate, NF | 4.00 |
| Alcohol Specially Denatured 23A 190 Proof | 35.00[1] |
| Purified Water, USP (Deionized) | 105.00 |

[1]Not present in the finished tablet product

Suspensions of the compositions of the present invention are prepared in a conventional manner such that each 5 mL (one teaspoon) would contain approximately 3 to 8 mg. of phenylephrine tannate and 50 to 150 mg of guaifenesin. Additionally, the suspension formulations may contain colorants, natural and artificial flavors, glycerin, kaolin, magnesium aluminum silicate, methylparaben, sorbic acid, benzoic acid, pectin, purified water, saccharin, sodium hydroxide and sucrose or sorbitol. Example 2, which follows, is illustrative of a typical suspension formulation of the present invention prepared by conventional well known compounding techniques.

EXAMPLE 2

| Phenylepherine Tannate and Guaifenesin Suspension | |
|---|---|
| Ingredient | Milligrams per 5 mL |
| Phenylephrine tannate | 5.00 |
| Guaifenesin | 100.00 |
| Pectin, USP (Medium Viscosity) | 50.00 |
| Kaolin USP (Colloidal Powder) | 1000.00 |
| Magnesium Aluminum Silicate, NF | 35.00 |
| Benzoic Acid, USP | 10.00 |
| Sorbic Acid, USP | 6.00 |
| Methylparaben, NF | 5.00 |
| Sucrose, NF | 1000.00 |
| Saccharin Sodium, USP | 2.00 |
| Glycerin, USP | 225.00 |
| Flavor Black Currant Imitation | 0.91 |
| Flavor Strawberry with Other Natural Flavors | 2.28 |
| FD&C Red #3 Dye | 1.60 |
| Sodium Hydroxide Solution-50% | 0.30[1] |
| Purified Water, USP (Deionized) adjust to | 5 mL |

[1]The quantity of Sodium Hydroxide Solution may be varied depending on the pH of the Kaolin used in the batch. Tannic acid may also be used in lieu of sodium hydroxide solution for pH adjustment. Sodium Citrate, USP, Dihydrate and Citric Acid, USP, Anhydrous may also be included in the formula for pH adjustment.

For the purpose of this disclosure, a warm-blooded animal is a member of the animal kingdom possessed of a homeostatic mechanism and includes mammals and birds.

The dosage administered will be dependent on the age, health and weight of the recipient, kinds of concurrent treatment, if any, frequency of treatment and effect desired.

It should be understood that the above examples are illustrative of the best mode only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A therapeutic composition for the symptomatic relief of cough associated with respiratory tract conditions such as the common cold, bronchial asthma, and acute and chronic bronchitis in warm-blooded animals in need of such treatment, said composition comprising pharmaceutically effective amounts of active ingredients, said active ingredients consisting of phenylephrine tannate and guaifenesin.

2. A therapeutic composition as claimed in claim 1 in tablet form.

3. A therapeutic composition as claimed in claim 1 in suspension form.

4. A method for symptomatically treating and relieving the distress of cough associated with respiratory tract conditions resulting from the common cold, bronchial asthma, and acute and chronic bronchitis in warm-blooded animals which comprises orally administering to a warm-blooded animal in need of such treatment a therapeutic amount of a composition comprising active ingredients, said active ingredients consisting of phenylephrine tannate and guaifenesin.

5. A method as claimed in claim 4 wherein said composition is in tablet form.

6. A method as claimed in claim 4 wherein said composition is a suspension.

7. The therapeutic composition of claim 2, wherein said tablet form contains about 20 to 30 mg. of phenylephrine tannate and about 100 to 300 mg. of guaifenesin.

8. The therapeutic composition of claim 2, wherein said tablet form contains about 25 mg. of phenylephrine tannate and about 200 mg. of guaifenesin.

9. The therapeutic composition of claim 3, wherein said suspension form contains about 3 to 8 mg. of phenylephrine tannate and about 50 to 150 mg. of guaifenesin, per 5 ml.

10. The therapeutic composition of claim 3, wherein said suspension form contains about 5 mg. of phenylephrine tannate and about 100 mg. of guaifenesin, per 5 ml.

11. The method of claim 5, wherein said tablet form contains about 20 to 30 mg. of phenylephrine tannate and about 100 to 300 mg. of guaifenesin.

12. The method of claim 5, wherein said tablet form contains about 25 mg. of phenylephrine tannate and about 200 mg. of guaifenesin.

13. The method of claim 6, wherein said suspension form contains about 3 to 8 mg. of phenylephrine tannate and about 50 to 150 mg. of guaifenesin, per 5 ml.

14. The method of claim 6, wherein said suspension form contains about 5 mg. of phenylephrine tannate and about 100 mg. of guaifenesin, per 5 ml.

* * * * *